United States Patent [19]
Carlsson et al.

[11] Patent Number: 5,225,596
[45] Date of Patent: Jul. 6, 1993

[54] HALO SUBSTITUTED AMINOTETRALINS

[75] Inventors: Per A. E. Carlsson, Gothenburg; Hakan V. Wikstrom, Partille; Kjell A. I. Svensson, Alingas; Bengt R. Andersson, Lindome; Barbro A. Ekman, Gothenburg; Nils P. Stjernlof, Angered; Nils A. Svensson, Molndal, all of Sweden

[73] Assignee: The Upjohn Company, Kalamazoo, Mich.

[21] Appl. No.: 721,532

[22] Filed: Jul. 8, 1991

Related U.S. Application Data

[63] Continuation of Ser. No. 295,169, Jan. 9, 1989, abandoned.

[51] Int. Cl.$^5$ .................. C07C 217/00; C07C 217/74; C07C 211/00; C07C 211/60
[52] U.S. Cl. .................... 564/428; 564/374; 549/79
[58] Field of Search .................. 549/75; 564/374, 428

[56] References Cited

U.S. PATENT DOCUMENTS

| | | | |
|---|---|---|---|
| 4,192,888 | 3/1980 | Bondinell et al. | 424/321 |
| 4,788,130 | 11/1988 | Oshiro et al. | 564/428 X |

FOREIGN PATENT DOCUMENTS

| | | |
|---|---|---|
| 893917 | 7/1981 | Belgium . |
| 41488 | 12/1981 | European Pat. Off. . |
| 52932 | 6/1982 | European Pat. Off. . |
| 272534 | 12/1987 | European Pat. Off. . |
| 1518652 | 4/1969 | Fed. Rep. of Germany . |
| 2333847 | 1/1974 | Fed. Rep. of Germany . |
| 2803582 | 8/1979 | Fed. Rep. of Germany . |
| 90/15047 | 12/1990 | PCT Int'l Appl. . |
| 637363A | 7/1983 | Switzerland . |
| 637364 | 7/1983 | Switzerland . |
| 1377356 | 12/1974 | United Kingdom . |
| 1597140 | 9/1981 | United Kingdom . |

OTHER PUBLICATIONS

Weinstock et al, J. Med. Chem., vol. 29 (1986) pp. 1615-1627.

DeMarinis et al, Chemical Abstracts, vol. 96 (1982) 51940w.
Hieble et al, Chemical Abstracts, vol. 97 (1982) 16659k.
Holz et al, Chemical Abstracts, vol. 98 (1983) 11098a.

(List continued on next page.)

Primary Examiner—Richard L. Raymond
Attorney, Agent, or Firm—Donald L. Corneglio

[57] ABSTRACT

This invention is therapeutically useful tetralins and pharmaceutically acceptable acid addition salts thereof of the formula

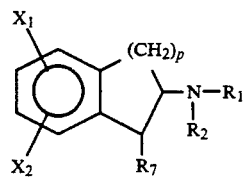

Formula I wherein $X_1$ is halogen, $CF_3$, $-OR_3$, or $-SR_4$; wherein $R_3$ is alkyl($C_1$-$C_8$); alkenyl($C_1$-$C_8$); $-CH_2$-cycloalkyl($C_3$-$C_8$) or benzyl; wherein $R_4$ is alkyl($C_1$-$C_3$); wherein $X_2$ is hydrogen, $CF_3$ or halogen; wherein $R_7$ is hydrogen or methyl; wherein $R_1$ is hydrogen, alkyl($C_1$-$C_3$), or cyclopropylmethyl; wherein $R_2$ is $-CH_2$-cycloalkyl($C_3$-$C_8$), alkyl($C_1$-$C_8$), $-(CH_2)_q-R_5$ or $-CH_2CH_2-Z-(CH_2)_r CH_3$; wherein $R_5$ is phenyl, 2-thiophene or 3-thiophene; wherein $Z$ is oxygen or sulfur; and wherein p is one or 2, q is 2 or 3, and r is zero to 3; with the provisos that (1) when $X_1$ is $-OR_3$, $X_2$ is halogen or $CF_3$; and (2) when $X_1$ is halogen, $X_2$ is hydrogen, and p is 2, $X_1$ is in a position other than the 8-position. These compounds are useful to treat central nervous system disorders.

9 Claims, No Drawings

OTHER PUBLICATIONS

Singh et al, Chemical Abstracts, vol. 100 (1984) 79479c.
Canon et al, J. Med. Chem., vol. 25 (1982) pp. 1442–1446.
Arvidsson et al, J. Med. Chem. vol. 27 (1984) pp. 45–51.
Ames, D. E., et al., J. Chem. Soc. 2636 (1965).
Arvidsson, L. E., et al., J. Med. Chem. 24, 921–923 (1981).
Arvidsson, L. E., J. Med. Chem. 30, 2105–2109 (1987).
Canon, J. G., et al., J. Med. Chem. 28, 515–518 (1985).
Dren, A. T., et al., J. Pharm. Sci. 67, 880–882 (1978).
McDermed, J. D., et al., J. Med. Chem. 18, 361–367 (1975).
McDermed, J. D., et al., J. Med. Chem. 19, 547–549 (1976).
Rusterholz, D. B., et al., J. Med. Chem. 19, 99–102 (1976).
Seeman, P., et al., Molecular Pharmacology 28, 291–299 (1985).
Wikstrom, H., et al., J. Med. Chem. 30, 1115 (1987).

HALO SUBSTITUTED AMINOTETRALINS

CROSS-REFERENCE TO RELATED APPLICATIONS

This application is a continuation of PCT/US90/00015, filed Jan. 3, 1990; which was a continuation of U.S. Ser. No. 07/295,169, filed Jan. 9, 1989, abandoned.

FIELD OF THE INVENTION

The present invention is related to novel 1,2,3,4-tetrahydro-2-naphthylamines and 2-indanylamines.

BACKGROUND OF THE INVENTION

Evidence from depressed patients indicates the neurotransmission in the central nervous system (CNS) may be disturbed. These disturbances involve the neurotransmitters noradrenaline (NA) and 5-hydroxytryptamine (5-HT). The drugs most frequently used in the treatment of depression are considered to act by improving the neurotransmission of either or both of these physiological agents. The mechanism of action for conventional drugs used to treat mental depression is generally believed to be indirect. It is thought the drugs block the reuptake of the neurotransmitters released from nerve terminals in the CNS, NA and/or 5-HT, which increases the concentration of these transmitters in the synaptic cleft and restores an adequate neurotransmission. For example, the clinically documented antidepression drug, zimelidine (dimethyl-amino-1-(4-bromophenyl)-1-(3-pyridyl)propene) acts as such a reuptake inhibitor with high selectivity for 5-HT neurons.

Available data suggests enhancement of 5-HT neurotransmission will primarily improve depressed mood and anxiety, whereas enhancement of noradrenaline neurotransmission will improve the retardation symptoms occurring in depressed patients. In recent years many efforts have been made to develop new drugs with high selectivity for the improvement of the 5-HT neurotransmission in the CNS.

A fundamentally different way to improve the neurotransmission in the central 5-HT neurons would be to use a 5-HT receptor agonist acting directly upon the 5-HT receptors, and particularly the 5-HT$_{1A}$ receptor. In order to minimize undesired side effects, a high selectivity for this kind of receptor would be necessary.

Clinically, 5-HT$_{1A}$ agonists have also demonstrated anxiolytic properties. The drug, Buspirone, is the only currently available marketed 5-HT$_{1A}$ agonist having anxiolytic activity. This compound antagonizes dopamine receptors at the same dose it stimulates 5-HT$_{1A}$ receptors. These dopamine antagonist properties reduce the clinical utility of these compounds however because long term treatment with dopamine antagonists can produce tardive dyskinesias.

The search for new CNS active compounds is focused on finding compounds with selective 5-HT$_{1A}$ receptor agonist effects without detrimentally influencing central dopamine receptors.

In recent years a large body of pharmacological, biochemical and electrophysical evidence has provided considerable support in favor of the existence of a specific population of central autoregulatory dopamine receptors located in the dopaminergic neuron itself and belonging to the D$_2$ receptor subclass of dopamine receptors. These receptors are part of a homeostatic mechanism that modulates nerve impulse flow and transmitter synthesis and regulates the amount of dopamine released from the nerve endings.

Drugs acting on central dopamine transmission are clinically effective in treating a variety of central nervous system disorders such as parkinsonism and schizophrenia. In parkinsonism, for example, the nigro-neostriatal hypofunction can be restored by an increase in postsynaptic dopamine receptor stimulation. In schizophrenia, the condition can be normalized by achieving a decrease in postsynaptic dopamine receptor stimulation. Classical antipsychotic agents directly block the postsynaptic dopamine receptor. The same effect can be achieved by inhibition of intraneuronal presynaptic events essential for the maintenance of adequate neurotransmission, transport mechanism and transmitter synthesis.

Direct dopamine receptor agonists, like apomorphine, are able to activate the dopamine autoreceptors as well as the postsynaptic dopamine receptors. The effects of autoreceptor stimulation appear to predominate when apomorphine is administered at low doses, whereas at higher doses the attenuation of dopamine transmission is outweighed by the enhancement of postsynaptic receptor stimulation. The antipsychotic and antidyskinetic effects in man of low doses of apomorphine are likely due to the autoreceptor-stimulator properties of this dopamine receptor agonist. This body of knowledge indicates dopamine receptor stimulants with a high selectivity for central nervous dopamine autoreceptors would be valuable in treating psychiatric disorders.

INFORMATION DISCLOSURE STATEMENT

The following documents could be important in the examination of this application.

Derwent 12191K (Belgium 893,917) discloses indanyl substituted imidazole derivatives and tetralyl imidazole derivatives wherein the aromatic ring of the indanyl and tetralyl groups may be substituted with various groups including halogen, alkyl (C$_1$–C$_6$, trihaloalkyl, alkoxy and alkylthio. The compounds are useful in treating atherosclerosis.

British Patent 1,377,356 discloses 8-hydroxy and 8-methoxy substituted-1,1-dialkyl-2-aminotetralins wherein the amino group is unsubstituted or substituted with an alkyl C$_1$–C$_6$. These compounds are useful as analgesics.

Derwent 40378A/23 (British 1,597,140) discloses, among other compounds, 2-aminotetralins substituted on the aromatic ring with halogen, di-chloro and additionally hydroxy or an alkanoyloxy group. These compounds are useful in treating heart conditions and/or Parkinson's disease.

Switzerland 637,363 (Derwent 729,386) and Switzerland 637,364 discloses, among other compounds, 2-aminotetralins substituted on the aromatic ring with halogen, di-chloro and additionally hydroxy, alkyl or other functional groups. These compounds are stimulants of α- and β-adrenergic and dopamine receptors rendering them useful in treating heart failure, cardiac infarct, hypertension and Parkinson's disease.

Germany 2,333,847 (Derwent 7633V) discloses a very broad scope of compounds which can include amino tetralins and amino indanes substituted on the aromatic ring with alkoxy or halogen and additionally hydroxy, aralkyloxy or acyloxy. These compounds are water softening agents and corrosion inhibitors in lubricants as well as CNS-depressants and anti-arrhythmics.

European 272,534-A (Derwent 88-176680) discloses 2-aminotetralins substituted in the 8-position by halogen (fluorine, chlorine, bromine or iodine) among many other compounds within a broad disclosure. These compounds are useful serotonin antagonists or agonists with high affinity for cerebral 5-HT[1] receptors rendering them useful in the treatment of CNS disorders, cognitive deficiencies, Alzheimer's disease, cardiovascular disorders, pain and intestinal disorders.

German 2803582 (Derwent 58247B) discloses 2-aminotetralins wherein the amino group is substituted with inter alia alkyl, or cycloalkyl and wherein the aromatic ring is substituted with inter alia alkyl, halogen, di-chloro and additionally with hydroxy or an alkanoyloxy group. These compounds have a stimulant effect on α- and β-adrenoreceptors and on dopamine receptors and are useful in the treatment of heart failure, cardiac infarct, elevated blood pressure and Parkinson's disease.

Wikstrom, H., et al., J. Med. Chem. 30, 1115 (1987) discloses 4-hydroxy- and 4-methoxy-2-aminoindanes wherein the amino moiety is unsubstituted or is substituted with dimethyl or di-n-propyl; 5-hydroxy-2-dimethylaminoindane; and 7-hydroxy-2-aminotetralin wherein the amino moiety is substituted with dimethyl or di-n-propyl. This paper focuses on the conformational analysis of the compounds in relation to their central dopaminergic effects.

J. G. Canon, et al., J. Med. Chem. 25, 1442–1446 (1982) and J. Med. Chem. 28, 515–518 (1985) disclose inter alia, 4-hydroxy- and 5-hydroxy-2-di-n-propylindane in a study dealing with the conformational analysis of a series of 2-aminoindans.

Seeman, et al., Molecular Pharmacology 28, 291–299 (1985) includes a number of known hydroxy substituted and methoxy substituted aminotetralins and aminoindans in a $D_2$ receptor binding affinity study.

A. T. Dren, et al., J. Pharm. Sci. 67, 880–882 (1978) discloses among other compounds 2-aminotetralin wherein the amino group is mono-substituted with cyclopropylmethyl or cyclopropyl and the aromatic ring is substituted with methoxy at the 5- or 6-position. These compounds were tested for local anesthetic activity.

D. E. Ames, et al., J. Chem. Soc. 2636 (1965) describes the synthesis of various di-alkoxy substituted aminotetralins wherein the alkoxy groups have from 1 to 4 carbon atoms. 6-Methoxy-2-aminotetralin is also described.

L. E. Arvidsson, J. Med. Chem. 27, 45–51 (1984) describes a series of 2-aminotetralins wherein the amine is substituted with one or two lower alkyl groups of 1–4 carbon atoms, octyl or benzyl, and the aromatic ring is substituted 5- and/or 8-position with hydroxy or lower alkoxy. These compounds were tested as dopamine and 5-hydroxytryptamine receptor agonists.

L. E. Arvidsson, et al., J. Med. Chem. 24, 921–923 (1981) discloses 8-methoxy-2-aminotetralins wherein the amino moiety is substituted with n-propyl, benzyl or di-n-propyl and 2-di-n-propylaminotetralins wherein the aromatic ring is substituted in the 5-, 6-, 7- or 8-position with hydroxy. These compounds were evaluated for their affect on dopaminergic and α-adrenergic receptors.

J. D. McDermed, et al., J. Med. Chem. 19, 547–549 (1976) discloses 5,6-dihydroxy and 5-, 6- and 7-hydroxy-2-di-n-propylaminotetralins in a study of their dopaminergic activity.

J. D. McDermed, et al., J. Med. Chem. 18, 362–367 (1975) discloses a large series of 2-aminotetralins wherein the aromatic ring is mono- or di-substituted with hydroxy, methyl or lower alkoxy and the amine moiety is unsubstituted or substituted with lower alkyl, benzyl, alkoxyalkyl or forms part of a monocyclic heterocyclic group. These compounds were evaluated for their dopaminergic activity.

L. E. Arvidsson, J. Med. Chem. 30, 2105–2109 (1987) evaluates the 5-HT receptor agonist activity of 1-methyl-2-di-n-propylaminotetralins substituted in the 8-position with hydroxy or methoxy.

D. B. Rusterholz, et al., J. Med. Chem. 19, 99–102 (1976) discloses 5- and/or 8-substituted-2-aminotetralins wherein the 5- or 8-position is substituted with methyl, hydroxy or methoxy. The effect of these compounds on prolactin release is evaluated.

J. G. Cannon, et al., J. Med. Chem. 28, 515 (1985) describes the resolution of 4-hydroxy-2-(di-n-propyl)aminoindane, a synthetic precursor to a potent dopaminergic agonist.

SUMMARY OF THE INVENTION

This invention encompasses compounds of Formula I (see Formula Chart) and pharmaceutically acceptable acid addition salts thereof, wherein $X_1$ is halogen, $CF_3$, $-OR_3$ or $-SR_4$; wherein $R_3$ is selected from the group consisting of alkyl($C_1$–$C_8$), alkenyl($C_1$–$C_8$), $-CH_2$-cycloalkyl($C_3$–$C_8$) or benzyl; wherein $R_4$ is alkyl($C_1$–$C_3$); wherein $X_2$ is hydrogen, $CF_3$ or halogen; wherein $R_7$ is hydrogen or methyl; wherein $R_1$ is hydrogen, alkyl($C_1$–$C_3$) or cyclopropylmethyl; wherein $R_2$ is $-CH_2$-cycloalkyl($C_3$–$C_8$), alkyl($C_1$–$C_8$), $-(CH_2)_q-R_5$ or $-CH_2CH_2-Z-(CH_2)_r CH_3$; wherein $R_5$ is phenyl, 2-thiophene or 3-thiophene; wherein $Z$ is oxygen or sulfur; wherein p is one or 2, q is 2 or 3, and r is zero to 3; with the proviso that (1) when $X_1$ is $-OR_3$, $X_2$ is $CF_3$ or halogen; (2) when $X_1$ is halogen, $X_2$ is hydrogen; and (3) p is 2, $X_1$ is in a position other than the 8-position. As used herein halogen means Cl, Br, or F.

As shown by Formula I the compounds of this invention are aminotetralin derivatives when p is 2 as represented by Formula II or are indane derivatives when p is one or represented by Formula III. In Formulas II and III the various substituent groups $X_1$, $X_2$, $R_1$, $R_2$ and $R_7$ have the meanings described in Formula I.

The compounds of this invention possess selective pharmacological properties and are useful in treating central nervous system disorders including depression symptoms, anxiety symptoms, panic attacks, obsessive-compulsive disturbances, senile dementia, emotional disturbances related to dementia disorders, and disturbances of sexual functions. The compounds of this invention are also useful to alleviate aggressive behavior, confusional delirious states and impotence.

According to a preferred embodiment, the invention is related to compounds of Formula I where $R_2$ is $-CH_2$-cycloalkyl ($C_3$–$C_8$). A more preferred embodiment are compounds of Formula I where $R_1$ is alkyl ($C_1$–$C_3$), $R_2$ is cyclopropylmethyl, and $X_1$ is halogen. Compounds of formula I wherein $R_7$ is hydrogen are also preferred.

An object of the invention is to provide compounds for therapeutic use, especially compounds having a therapeutic activity in the central nervous system. Another object is to provide compounds having an effect on the 5-HT$_{1A}$ receptor in mammals including man. A further object of this invention is to provide compounds having an effect on the subclass of dopamine receptors known as the D$_2$ receptor.

The pharmaceutical use and pharmaceutical preparations employing the compounds of Formula I constitute further aspects of the invention.

DETAILED DESCRIPTION OF THE INVENTION

The compounds of this invention are identified in two ways: by the descriptive name and reference to labelled structures contained in Formula Charts.

As used herein the parenthetical term $(C_n-C_m)$ is inclusive such that a compound of $(C_1-C_8)$ would include compounds of one to 8 carbons and their isomeric forms. The various carbon moieties are defined as follows: Alkyl refers to an aliphatic hydrocarbon radical and includes branched or unbranched forms such as methyl, ethyl, n-propyl, isopropyl, n-butyl, isobutyl, sec-butyl, t-butyl, n-pentyl, isopentyl, neo-pentyl, n-hexyl, isohexyl, n-heptyl, isoheptyl, and n-octyl. Alkoxy as represented by —OR$_3$ when R$_3$ is alkyl(C$_1$-C$_8$) refers to an alkyl radical which is attached to the remainder of the molecule by oxygen and includes branched or unbranched forms such as methoxy, ethoxy, n-propoxy, isopropoxy, n-butoxy, isobutoxy, sec-butoxy, t-butoxy, n-pentoxy, isopentoxy, neo-pentoxy, n-hexoxy, iso-hexoxy, n-heptoxy, isoheptoxy, and n-octoxy. Alkenyl refers to a radical of an aliphatic unsaturated hydrocarbons having a double bond and includes both branched and unbranched forms such as ethenyl, 1-methyl-1-ethenyl, 1-propenyl, 2-propenyl, 1-butenyl, 2-butenyl, 3-butenyl, 2-methyl-1-butenyl, 1-pentenyl, 2-pentenyl, 3-pentenyl, 4-pentenyl, 1-methyl-4-pentenyl, 3-methyl-1-pentenyl, 3-methyl-2-pentenyl, 1-hexenyl, 2-hexenyl, 3-hexenyl, 4-hexenyl, 1-methyl-4-hexenyl, 3-methyl-1-hexenyl, 3-methyl-2-hexenyl, 1-heptenyl, 2-heptenyl, 3-heptenyl, 4-heptenyl, 1-methyl-4-heptenyl, 3-methyl-1-heptenyl, 3-methyl-2-heptenyl, 1-octenyl, 2-octenyl, or 3-octenyl. Cycloalkyl refers to a radical of a saturated cyclic hydrocarbon such as cyclopropyl, cyclobutyl, cyclopentyl, cyclohexyl, cycloheptyl, or cyclooctyl. Halogen refers to a radical of fluorine, chlorine, bromine or trifluoromethyl, i.e., CF$_3$. The group —SR$_4$ is representative of methylthio, ethylthio and propylthio substituent groups.

It will be apparent to those skilled in the art that compounds of this invention may contain chiral centers. The compounds of Formula I contain asymmetric carbon atoms in the aliphatic ring moiety, including the ring carbon atoms adjacent to the nitrogen atom. The therapeutic properties of the compounds may to a greater or lesser degree depend on the stereochemistry of a particular compound. The scope of this invention includes all enantiomeric or diastereomeric forms of Formula I compounds either in pure form or as mixtures of enantiomers or diastereomers. Pure enantiomers as well as enantiomeric or diastereomeric mixtures are within the scope of the invention.

Both organic and inorganic acids can be employed to form nontoxic pharmaceutically acceptable acid addition salts of the compounds of this invention. Illustrative acids are sulfuric, nitric, phosphoric, hydrochloric, citric, acetic, lactic, tartaric, pamoic, ethanedisulfonic, sulfamic, succinic, cyclohexylsulfamic, fumaric, maleic, and benzoic acid. These salts are readily prepared by methods known in the art.

The compounds of this invention may be obtained by one of the following methods described below and schematically outlined in Chart I. The compounds of this invention are prepared by various means all of which involve reactions which are well known in the art. To prepare compounds wherein R$_1$ is hydrogen, ethyl or propyl and wherein R$_2$ is —CH$_2$-cycloalkylC$_5$-C$_8$, alkyl C$_2$-C$_8$, —(CH$_2$)$_q$—R$_5$ or —CH$_2$CH$_2$O(CH$_2$)$_r$CH$_3$, a compound of the formula C-1 (see Chart I) is treated with an appropriate acid halide, e.g., an acid chloride, of the formula R$_y$COhalide, wherein R$_y$ is cycloalkylC$_5$-C$_8$, alkylC$_1$-C$_7$, —(CH$_2$)$_r$—R$_5$ or —CH$_2$O—(CH$_2$)$_r$CH$_3$ wherein t is 1 or 2 and r is 0-3 to give a compound of formula C-2. In the structures or formulas set forth in Chart I the substituents L$_1$ and L$_2$ are protecting groups known in the art which can be sequentially and selectively removed to give hydroxy groups. The amide of formula C-2 is converted to the hydroxy amide compounds of formula C-3 by selective removal of the protecting group L$_2$ by, for example, treatment with 48% HBr under nitrogen gas for 3 hours at 120° C. or by treatment with an inorganic base, such as, sodium hydroxide or potassium hydroxide in an aqueous lower alcoholic solvent such as aqueous methanol, ethanol, or n-butanol at reflux for ½ hour to 12 hours. The C-3 hydroxy amide compounds are then converted to amine amide compounds, C-4, by using methods well known in the art, and the amine is subsequently converted to hydrogen, chlorine or bromine by using the well known Sandmeyer reaction to give compounds of formula C-5. In formula C-5 the group X$_3$ is hydrogen, chlorine, or bromine. The bromine group of the formula C-5 compounds can be converted to a trifluoromethyl substituent by treatment with sodium trifluoroacetate and copper iodide in DMPU at 160° C. for 4 hours under argon. The corresponding fluoro-substituted compounds can be prepared by diazotization of the amine of C-4 using diazonium hexafluorophosphate by procedures well known in the art. A preferred process for transforming the hydroxy moiety of formula C-3 compounds to the amine of C-4 compounds is described in Feiser and Feiser, Reagents in Orgnaic Synthesis, 4:86-87, and Sherrer and Beatty, J. Org. Chem. 37, 1681 (1972). The compounds of formula C-5 are converted to formula C-6 compounds by selectively removing the remaining L$_1$ protecting group and alkylating the hydroxy group with an appropriate alkylating reagent or conversion of the hydroxy to an amine and subsequently to chlorine or bromine as described above. To react the hydroxy moiety with an appropriate alkylating agent, the deprotected hydroxy compound may be treated with an alkyl halide or tosylate R$_b$X wherein R$_b$ is alkylC$_1$-C$_8$, alkenylC$_1$-C$_8$, —CH$_2$-cycloalkylC$_3$-C$_8$ or benzyl and wherein X or the halide is Cl, Br, I, TsO, in an organic solvent such as acetonitrile or acetone and in the presence of a base such as potassium carbonate or sodium hydroxide. It is readily apparent that the compounds of formula C-6 wherein X$_1$ and X$_2$ are halogen may be obtained by removing the L$_1$ and L$_2$ protecting groups to give the dihydroxy compound followed by conversion to the diamine and subsequently the dihalogen compounds.

The compounds of formula C-6 can be converted to the compounds of formula C-7 wherein R$_6$ is —CH$_2$ cycloalkylC$_5$-C$_8$, alkylC$_2$-C$_8$, —(CH$_2$)$_q$—R$_5$ or —CH$_2$CH$_2$O(CH$_2$)$_r$CH$_3$ by mixed hydride reduction using, for example, lithium aluminum hydride in ether or tetrahydrofuran, sodium borohydride in acetic or trifluoroacetic acid, diborane in tetrahydrofuran or QBH$_4$ in a mixture of dichloromethane and dichloroethane wherein Q represents tetrabutylammonium ion. The reagent QBH$_4$ is especially preferred when the amide compound is substituted on the aromatic ring with halogen and in particular bromine. The compounds of C-7 are final products of the invention and also can be used to prepare compounds of the invention therein R$_2$ is alkyl (C$_2$-C$_3$) by treatment with an acid halide, e.g., an acid chloride, of the formula R$_x$CO halide wherein R$_x$ is methyl or ethyl to give compounds of formula C-18. The compounds of formula C-18 are converted to compounds of Formula I wherein R$_1$ is ethyl or propyl by mixed hydride reduction as described above.

To prepare compounds of Formula I wherein R$_1$ is cyclopropylmethyl and R$_2$ is cyclopropylmethyl or cyclobutylmethyl a compound of formula C-1 is subjected to the treatments described in steps 2 to 5 as outlined in Chart I. Summarily a compound of formula C-1 is treated to selectively remove the L$_2$ protecting group to give the hydroxy substituted compound which is converted to an amine substituted and subsequently a halo substituted compound. The halo substituted compound is then treated to remove the L$_1$ protecting group and the resulting hydroxy substituted compound is treated either with an appropriate alkylating reagent or is converted to an amine, then a halo group as described above to give compounds of formula C-8. The compounds of formula C-8 are converted to compounds of Formula I wherein R$_1$ is cyclopropylmethyl and R$_2$ is cyclopropylmethyl or cyclobutylmethyl by treatment with an appropriate cycloalkyl acid halide with subsequent reduction of the resulting amide by hydride reduction methods as generally described hereinabove.

To prepare compounds of Formula I wherein R$_1$ or R$_2$ is methyl a compound of formula C-1 is treated with methyl iodide to give the corresponding monomethylated compound or is treated with formaldehyde in water in the presence of NaBH$_3$CN and a few drops of glacial acetic acid at pH5 to give the corresponding dimethylated compounds. The resulting mono- or dimethylated compounds are then subjected to the treatment described in steps 2 through 5 of Chart I to give compounds of Formula I wherein R$_1$ or R$_2$ is methyl.

To obtain compounds of Formula I wherein R$_2$ is —CH$_2$CH$_2$S(CH$_2$)$_r$CH$_3$ a ketone of formula C-9 is reacted with an alkylthioalkylamine of the formula H$_2$NCH$_2$CH$_2$S(CH$_2$)$_r$CH$_3$ wherein r is 0 to 3 in the presence of NaBH$_3$CN to give compounds of formula C-10. The compounds of formula C-10 are then subjected to the treatment described in steps 2 through 5 to give compounds of formula C-11 which are final products of this invention as represented by Formula I compounds. The compounds of formula C-11 can be converted to compounds of Formula I wherein R$_1$ is alkylC$_{1-3}$ or cyclopropylmethyl by appropriate treatment with an acid halide as described hereinabove in converting compounds of formula C-6 to formula C-7 compounds followed by mixed hydride reduction or by treatment with methyl iodide as described hereinabove.

To obtain compounds of Formula I wherein X$_2$ is hydrogen one need only replace the starting compounds of formula C-1 with corresponding compounds wherein the aromatic ring is substituted only with L$_1$O.

The compounds of formula C-1 or the corresponding compounds wherein the aromatic ring is substituted only with L$_1$O are obtained by treatment of the known or commercially available ketone of formula C-12, wherein R$_8$ is hydrogen or L$_1$O as defined hereinabove, with hydroxylamine in the presence of a base to give the intermediate oxime which is reduced to the corresponding amine by catalytic hydrogenation.

A pure enantiomer of a compound of Formula I may be prepared by converting the secondary amine of an appropriate final product of Formula I or an intermediate thereto as described in Chart I or as set forth in the Formula Chart into the (—)-O-methylmandelic acid amide followed by chromatographic separation of the two diastereomers and cleavage by subsequent reaction with potassium tert-butoxide in tetrahydrofuran with traces of water and methyl lithium. In the case of an incomplete reaction, the intermediate N-formyl derivative can be cleaved by the addition of methyl lithium to an ether solution of the formancide and subsequently quench with water and ether extraction to give the secondary amine. The secondary amine can be converted into the tertiary amine using methods already described.

In clinical practice the compounds of the present invention will normally be administered orally, rectally, or by injection, in the form of pharmaceutical preparations comprising the active ingredient either as a free base or as a pharmaceutically acceptable non-toxic, acid addition salt, such as the hydrochloride, lactate, acetate, sulfamate salt, in association with a pharmaceutically acceptable carrier. The use and administration to a patient to be treated in the clinic would be readily apparent to a person of ordinary skill in the art.

In therapeutical treatment the suitable daily doses of the compounds of the invention are 1-2000 mg for oral application, preferentially 50-500 mg, and 0.1-100 mg for parenteral application, preferentially 0.5-50 mg. The daily dosage will preferably be administered in divided dosages one to 4 times daily and the dosage amounts are based on an individual having a weight of about 70 kg.

The compounds of this invention where X$_1$ is in the 8-position when p is 2 on the aromatic ring are very selective 5-HT$_{1A}$ receptor agonists without having any dopaminergic activity. These compounds would be particularly effective anxiolytic and antidepressant agents. Other uses for these compounds include panic attacks, obsessive-compulsive disturbances, and senile dementia particularly the emotional disturbances seen in dementia disorders. In addition, central 5-HT receptor activation are believed to be involved in mediating the sexual behavior. These compounds would be useful to stimulate sexual activity and to alleviate impotence.

The compounds of this invention where X$_1$ is in the 5-position when p is 2 on the aromatic ring are selective D$_2$ autoreceptor agonists. These compounds would be particularly effective antipsychotic agents and useful in treating Parkinson's disease.

The compounds of this invention where R$_2$ is cycloalkylmethyl also have high oral potency and a long duration of action. Both these features are beneficial to effective clinical treatment.

The utility of the compounds of this invention to treat central nervous system disorders is shown in behavioral and biochemical activity in reserpine-pretreated rats.

Depletion of CNS monoamine stores with reserpine brings about a "neuroleptic syndrome" characterized by hypomotility, catalepsy, muscle rigidity, hunchbacked posture as well as a number of other central and peripheral signs of monoamine depletion. The whole or parts of this syndrome can be reversed by the administration of drugs that stimulate DA or 5-HT receptors directly or indirectly.

Stimulation of the DA receptors, with apomorphine for example, gives rise to both locomotion and stereotyped behavior such as sniffing, gnawing and jumping. On the other hand, stimulation of the 5-HT receptors, with 5-hydroxytryptophan (5-HTP) combined with MAO-inhibitors for example, gives rise to a very different behavior. The animals lie flat on the cage floor exhibiting forward movements with extended forepaws padding, "piano-playing," and abducted hindlegs, occasionally with some tremor in the forebody and with Staubtail, stiff tail erection.

The compounds under evaluation are tested biochemically for central DA- and 5-HT receptor (pre- and/or postsynaptic) stimulating activity. The concept of this biochemical screening method is that a DA- or 5-HT-receptor agonist will stimulate the receptor and through regulatory feedback systems effect a decline in tyrosine or tryptophan hydroxylating activity, respectively, and a subsequent reduction in the synthesis rate for DA and 5-HT in the presynaptic neuron. Dopa and 5-HTP formation, as determined after in-vivo inhibition of the aromatic L-amino acid decarboxylase with NSD 1015 (3-hydroxybenzylhydrazine hydrochloride) are taken as indirect measures of DA- and 5-HT-synthesis rates, respectively as described by H. Wikstrom, et al., J. Med. Chem. 27, 1030 (1984).

The following detailed examples describe how to prepare the various compounds and/or perform the various processes of the invention and are to be construed as merely illustrative, and not limitations of the preceding disclosure in any way whatsoever. Those skilled in the art will recognize appropriate variations from the procedures both as to reactants and as to reaction conditions and techniques.

EXAMPLES

Example 1

5-Bromo-8-methoxy-2-(di-n-propylamino)tetralin (OSU641)

8-Methoxy-2-(di-n-propylamino)tetralin.HCl (200 mg; 0.67 mmol) was dissolved in absolute EtOH (20 ml) and $Br_2$ (0.6 ml of a solution of 0.3 ml $Br_2$ in $CH_2Cl_2$ (1:1)) was added under stirring at 0° C. The reaction was complete after 2 hours at that temperature according to GLC analysis (capillary GC at 220° C. isothermal gave $R_t$=435 min). The solvents were removed under reduced pressure and the residue was dissolved in absolute EtOH and HCl-saturated EtOH was added. Evaporation gave an oil, which was dissolved in EtOH. Addition of ether gave crystals (224 mg) after cooling in a $CO_2$/EtOH bath. GC-MS (250° C. isothermal) gave the product at $R_t$=2.56 min with the M+/M+2 at m/e=339.10(10.4%)/341.10(9.0%).

Example 2

8-Bromo-5-methoxy-2-(di-n-propylamino)tetralin (OSU646)

5-Methoxy-2-(di-n-propylamino)tetralin.HCl (150 mg; 0.50 mmol) was dissolved in absolute EtOH (7 ml) and $Br_2$ (1 ml of a solution of 0.35 ml $Br_2$ in 9.65 ml EtOH) was added under stirring at −10° C.-0° C. The reaction was complete after 2 hours at that temperature according to GLC analysis (capillary GC at 250° C. isothermal gave $R_t$=3.53 min). The solvents were removed under reduced pressure and the residue was dissolved in absolute EtOH and HCL-saturated EtOH was added. Evaporation gave a brown oil, which was dissolved in $CH_2Cl_2$. Addition of ether gave crystals (60 mg). GC-MS (250° C. isothermal) gave a product at $R_t$=2.56 min with the M+/M+2 at m/e=339/341.

Example 3

4-Bromo-7-methoxy-2-(di-n-propylamino)indane (OSU648)

4-Methoxy-2-(di-n-propylamino)indane.HCl (155 mg; 0.55 mmol) was dissolved in absolute EtOH (20 ml) and $Br_2$ (0.3 ml of a solution of $Br_2$ in $CH_2Cl_2$ (1:1)) was added under stirring at room temperature. The reaction was complete after 2 hours at that temperature according to GLC analysis (capillary GC at 250° C. isothermal gave $R_t$=2.37 min). The solvents were removed under reduced pressure and the residue was dissolved in absolute EtOH and HCl-saturated EtOH was added. Evaporation gave an oil, which was dissolved in absolute EtOH and crystals were formed. These were washed with ether and centrifugation gave 100 mg crystals. GC-MS (250° C. isothermal) gave the product at $R_t$=1.70 min with the M+/M+2 at m/e=325.00(5.6%)/327.10 (4.7%) and the base peak pair at m/e=296.00(100%)/298.00(96.3%).

Example 4 cis-1S,2R-8-Bromo-5-methoxy-1-methyl-2-(di-n-propylamino)tetralin (OSU491)

cis-1S,2R-5-Methoxy-1-methyl-2-(di-n-propylamino)tetralin.HCl (100 mg; 0.37 mmol) was dissolved in absolute EtOH (15 ml) and $Br_2$ (1.5 ml of a solution of 0.16 ml $Br_2$ in 10 ml $CH_2Cl_2$ was added under stirring at room temperature. The reaction was complete after 2 hours at that temperature according to GC analysis (capillary GAC at 250° C. isothermal gave $R_t$=3.6 min). The solvents were removed under reduced pressure and the residue was basified with 10% $Na_2CO_3$ and extracted with $CH_2Cl_2$. The residue after drying ($Na_2SO_4$) filtration and evaporation was chromatographed ($SiO_2$) and the fractions containing pure product were pooled and evaporation yielded 78 mg of an oil, which was dissolved in absolute EtOH, and HCl-saturated EtOH was added. Evaporation gave an oil from which no crystals were obtained GC-MS (250° C. isothermal) gave the product at $R_t$=2.62 min with the M+/M+2 at m/e=353.10(12.6%)/355.10(10.7%). The base peak pair appeared at m/e=324.10(96.1%)/326.10(100.0%).

Example 5 cis-1S,2R-5-Bromo-8-methoxy-1-methyl-2-(di-n-propylamino)tetralin (OSU493)

cis-1S,2R-8-Methoxy-1-methyl-2-(di-n-propylamino)tetralin.HCl (29 mg; 0.093 mmol) was dissolved in absolute EtOH (5 ml) and $Br_2$ (1.5 ml of a solution of 0.054 ml $Br_2$ in 10 ml $CH_2Cl_2$) was added under stirring at room temperature. The reaction was complete after 2 hours at that temperature according to GLC analysis (capillary GC at 180°-280° C.; 16° C./min gave $R_t$=6.01 min). The solvents were removed under reduced pressure and crystals were obtained from EtOH/ether (34 mg) and melting at 193°-198° C. GC-MS (250° C. isothermal) gave the product at $R_t$=2.58 min with the M+/M+2 at m/e=353.10(12.6%)/355.10 (11.0%) and the base peak at m/e=174.10. Other peaks at m/e=324.10 (92.1%)/326.10(85.8%).

Example 6

5-Bromo-8-methoxy-2-(di-cyclopropymethylamino) tetralin (OSU327)

8-Methoxy-2-(di-cyclopropylamino)tetralin.HCl (160 mg; 0.50 mmol) was dissolved in absolute EtOH (25 ml) and excess Br$_2$ (of a solution of 0.1 ml Br$_2$ in 10 ml CH$_2$Cl$_2$) was added under stirring at room temperature. The reaction was complete after 2 hours at that temperature according to GLC analysis (capillary GC at 250° C.; 16° C./min gave R$_t$=6.47 min). The solvents were removed under reduced pressure and the brownish residual oil was partitioned between 10% Na$_2$CO$_3$ and CH$_2$Cl$_2$. The organic layer was dried, filtered and the solvent was evaporated, yielding an oil (178 mg) which contained both the product (62%) and the monoalkylated analog (38%). The pure product was obtained after chromatography (SiO$_2$; acetone) and the residual oil, after evaporation of the solvent, was converted to the hydrochloride with HCl-saturated EtOH. Crystals were obtained from EtOH/ether. GC-MS (250° C. isothermal) gave the product at R$_t$=4.64 min with the M+/M+2 at m/e=363.15(46.5%)/365.25(44.9%).

Example 7

(−)-5-Bromo-8-methoxy-2-(dicyclopropylmethylamino)tetralin ((−)-OSU327)

8-Methoxy-2-(di-cyclopropylmethylamino)tetralin (OSU427) (311 mg, 1.09 mmol) was brominated in EtOH with 1.5 ml of a solution containing 0.6 ml Br$_2$ in 10 ml CH$_2$Cl$_2$). After night in room temperature, the solvent was evaporated and the raw product (HBr salt) was recrystallized from acetone/ether to give 311 mg of white crystals melting at 153°–154° C. $\alpha_D^{20} = -51.2°$. GC/MS shows M+/M+2 at m/e=363.10 (43.1%) and 365.00 (41.9%) and the base peak at m/e=160.05.

Example 8

5-Bromo-8-methoxy-2-(cyclopropylmethylamino)tetralin (OSU328)

8-Methoxy-2-(cyclopropylamino)tetralin as the base (200 mg, 0.70 mmol) was dissolved in absolute EtOH (25 ml) and excess Br$_2$ (of a solution of 0.1 ml Br$_2$ in 10 ml CH$_2$Cl$_2$) was added under stirring at room temperature. The reaction was complete after 0.5 hours at that temperature according to GC analysis (capillary GC at 250° C.; 16° C./min gave R$_t$=3.29 min). The solvents were removed under reduced pressure and the brownish residual oil was partitioned between 10% Na$_2$CO$_3$ and CH$_2$Cl$_2$. The organic layer was dried, filtered and the solvent was evaporated, yielding an oil which contained the product, which was converted to the hydrochloride with HCl-saturated EtOH. Crystals were obtained from EtOH/ether (115 mg) and melting at 279°–281° C. GC-MS (250° C. isothermal) gave the product at R$_t$=2.42 min with the M+/M+2 at m/e=309.00(36.5%)/311.00(34.9%).

Example 9

5- and 7-Bromo-2-tetralone m-Bromo-phenylacetic acid (3.4 g, 16 mmol) was dissolved in CH$_2$Cl$_2$ (10 ml) and SOCl$_2$ (1.5 ml, 2.8 g, 24 mmol) was added and the mixture was refluxed for 1.5 hours. Evaporation of the solvent and excess SOCl$_2$ gave the acid chloride, which was dissolved in CH$_2$CL$_2$ (10 ml) and added dropwise during 20 minutes to a mixture of 9.2 g (69 mmol) AlCl$_3$ in CH$_2$Cl$_2$ (200 ml) at about −5° C. Ethene gas was bubbled through the reaction mixture during 2 hours. The reaction was quenched by the slow addition of ice-water (75 ml). The phases were separated and the organic layer was washed once with 10% HCl and three times with 10% Na$_2$CO$_3$. The organic phase was dried (Na$_2$SO$_4$), filtered and the solvent was evaporated. The residual oil was dissolved in EtOH-water and added to a water solution of Na$_2$S$_2$O$_5$ (4.1 g). The bisulfite adduct was precipitated, filtered and dried (6.2 g).

Prior to separation the bisulphite adduct was dissolved in water and basified with 2M NaOH followed by 3 times extraction with ether. The organic layers were dried (Na$_2$SO$_4$), filtered and evaporated giving 2.5 g of crude material. The two isomers were separated on a silical column using petroleum ether/ether (3:1) giving 0.52 g of OSU71A (5-bromo-2-tetralone) followed by 1.37 g of OSU71B (7-bromo-2-tetralone). The isomers were identified by $^1$H-NMR in the aromatic region (OSU71A: δ 7.1 (two d, j$_1$=4, j$_2$=6, 2H), 7.49 (t, 1H); OSU71B: δ 7.12 (d, 1H), 7.29 (S 1H), 7.35 (q, j$_1$=8, j$_2$=2, 1H).

Example 10

5,6,7 or 8-Amino-2-(di-n-propylamino)tetralin

A stirred solution (9.2 ml) of 0.92M MeLi in ether (8.5 mmol) of methoxylamine in hexane (9 ml) was added dropwise (1 drop/s) followed by 2.6 ml (4.3 mmol) of a 1.55M solution of 5, 6, 7 or 8-lithio-2-(di-n-propylamino)tetralin (prepared from 5, 6, 7 or 8-bromo-2-(di-n-propylamino)tetralin and n-BuLi). The mixture was warmed to −15° C. for 2 hr and quenched with water (0.5 ml). Workup of the resulting mixture afforded the desired 5, 6, 7 or 8-amino-2-(din-propylamino)tetralin.

Example 11

5,6,7 or 8-Trifluoromethyl-2-(di-n-propylamino)tetralin

A mixture of 5,6,7 or 8-bromo-2-(di-n-propylamino)-tetralin (5 mmol), sodiumtrifluoroacetate (20 mmol) and copper (1)iodide (10 mmol) in 1,3-dimethyl-3,4,5,6-tetrahydropyridmidine (DMPU; 40 ml) was heated (160° C.) under Ar(g) for 4 hr. Workup of the reaction mixture afforded the 5,6,7 or 8-trifluoromethyl-2-(di-n-propylamino)tetralin in 70% yield (GC-analysis). As a specific example, the 8-CF$_3$ isomer was documented with GC/MS to have M+ at m/e=299.15(5.8%) and base peak at m/e=270.15 (M-29).

Example 12

5,6,7 or 8-Methylthio-2-(di-n-propylamino)tetralin.

A solution of 5,6,7 or 8-bromo-2-(di-n-propylamino)-tetralin (1.4 g; 4.5 mmol) in dry ether (20 ml) was cooled to −78° C. under nitrogen atmosphere. S-BuLi (7 ml, 10 mmol) was added and the mixture was stirred for 1 hr. Methylsulphide (0.31 g; 5 mmol) was added and the mixture was stirred for 3 hr. When the temperature reached −10° C., water was added. Workup afforded the product.

Example 13

(a) 5, and 7-Bromo-2-tetralone m-Bromo-phenylacetic acid (3.4 g, 15.8 mmol) was dissolved in CH$_2$Cl$_2$ (10 ml) and SOCl$_2$ (1.5 ml) was added and the mixture was refluxed for 1.5 hr. Evaporation of the solvent and excess SOCl$_2$ gave the acid chloride, which was dissolved in CH$_2$Cl$_2$ (25 ml) and added dropwise during 20 min to a mixture of AlCl$_3$ (9.2 g; 69.0 mmol)) in CH$_2$Cl$_2$ (200 ml) at about −5° C. Ethene gas was bubbled through the reaction mixture during 2–3 hr. The reaction was quenched by the slow addition of ice water (75 ml). The phases were separated and the organic layer was washed once with 10% HCl and three times with 10% Na$_2$CO$_3$. The organic phase was dried (Na$_2$SO$_4$), filtered and the solvent was evaporated. The residual oil was dissolved in EtOH-water and added to a water solution of Na$_2$S$_2$O$_5$ (4.0 g). The bisulfite adduct was precipitated, filtered, washed with acetone and dried (6.2 g). GC/MS showed M$^+$/M+2 at m/e=224 (65%) for both isomers. The bisulphite adduct was treated with 10% Na$_2$CO$_3$ and the ketone was extracted with ether to give 2.5 g after evaporation of the solvent. The mixture of the two ketones (5- and 7-bromo-2-tetralone) was separated by chromatography (SiO$_2$) and eluting with p-ether/di-i-ether; 3/1), yielding 0.52 g of isomer 1 (89% and 11% of isomer 2) and 1.37 g of isomer 2 (99% and 1% of isomer 1). NMR analysis assigned isomer 1 and isomer 2 to be 5-bromo-2-tetralone and 7-bromo-2-tetralone, respectively.

(b) 5-Bromo-2-(di-n-propylamino)tetralin

5-Bromo-2-tetralone (0.47 g (89%) from the chromatography above) was dissolved in benzene (150 ml) and p-toluolsulphonic acid (36 mg) and di-n-propylamine (1.8 ml) was added. The mixture was refluxed for 48 hr in a Dean-Stark apparatus under water separation. The solvent was removed and the residue was redissolved in MeOH (75 ml), and NaBH$_3$CN (1.9 g) was added and the mixture was stirred at room temperature for 2 hr. The solvents were removed under reduced pressure and the residue was redissolved in CH$_2$Cl$_2$ (100 ml) and washed with water and then 15% NaOH. The organic layer was separated, dried, filtered and the solvents were evaporated, yielding 0.59 g of the product, which was chromatographed (SiO$_2$ and eluting with EtOAc), yielding 0.4 g of the product as the base, which was converted to its hydrochloride with HCl-saturated EtOH. Evaporation and crystallization from EtOH/ether gave 0.39 g crystals melting at 151°–156° C. GC/MS showed M$^+$/M+2 at m/e=309(10%)/311(10%) and base peak at m/e=130).

(c) 7-Bromo-2-(di-n-propylamino)tetralin

The 7-bromo isomer was synthesized from 1.3 g of the 7-bromotetralone in accordance with its 5-bromo isomer above, yielding 1.03 g of the hydrochloride salt as crystals melting at 172°–176° C. GC/MS showed M$^+$/M+2 at m/e=309(10%)/311(10%) and base peak at m/e=130).

Example 14

(a) 7-Diazonium-8-methoxy-2-(di-n-propylammonium)tetralin bis(hexafluorophosphate) (3). Method III. Diazotization of the aniline derivative 7-Amino-8-methoxy-2-(di-n-propylamino)tetralin (0.27 g, 0.77 mmol) and precipitation of the corresponding diazonium hexafluorophosphate was performed according to a literature procedure (Rutherford, K. G.; Redmond, W. Organic Synthesis, V, 133). Yield 0.41 g (91%) of a colorless precipitate after drying at room temperature under pump vacuum overnight: mp 105°–110° C. (dec.).

(b) 7-Fluoro-8-methoxy-2-(di-n-propylamino)tetralin

The diazonium hexafluorophosphate (3) (0.35 g, 0.6 mmol) was pyrolyzed under pump vacuum at 190° C. (oil bath) 1.25 hr to give tary residue which was partitioned between 10% Na$_2$CO$_3$ (25 ml) and ether (25 ml). The water phase was extracted with ether (3×25 ml). The organic extract (100 ml) was dried (Na$_2$SO$_4$) and evaporated to give a yellow oil which was flash chromatographed (SiO$_2$/light petroleum ether:ethyl acetate:triethylamine 89:10:1). Yield 62 mg (27%) of a colorless oil.

FORMULA CHART

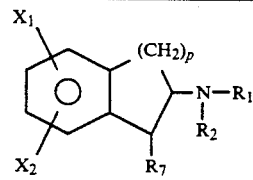

Formula I

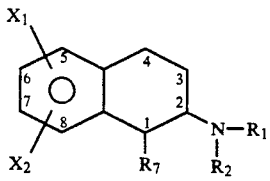

Formula II

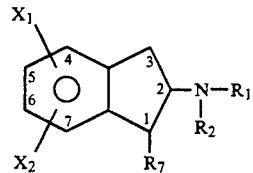

Fomrula III

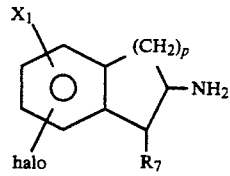

C-8

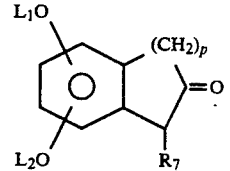

C-9

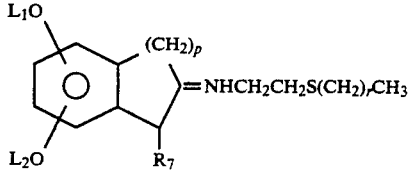

C-10

FORMULA CHART

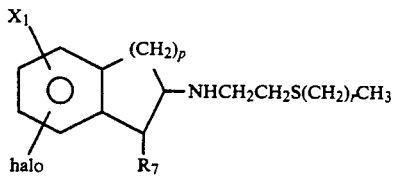

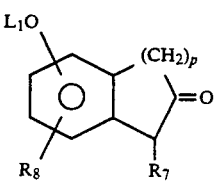 C-12

CHART I

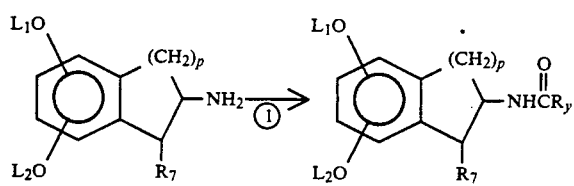

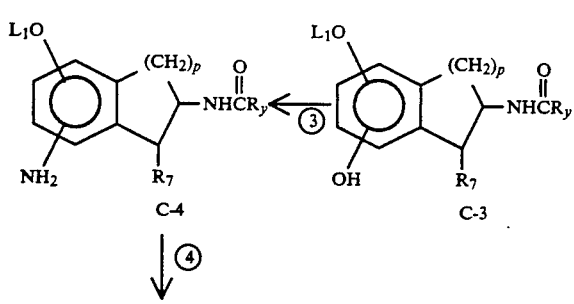

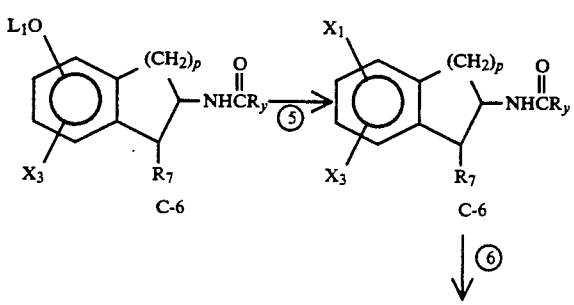

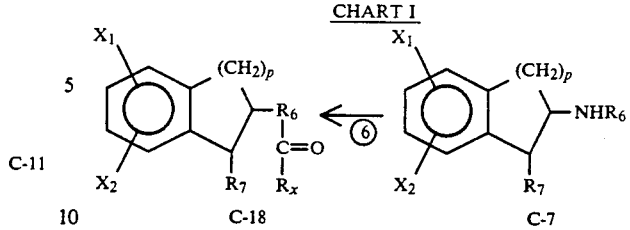

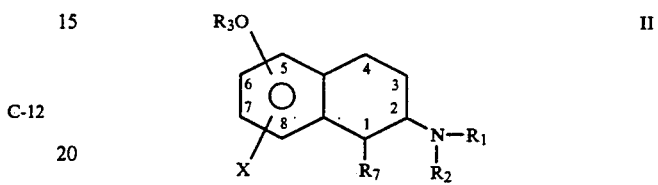

We claim:

1. A compound of formula II

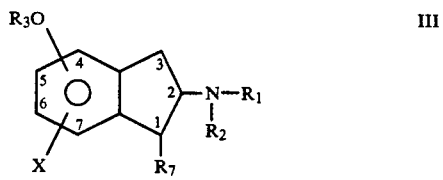

wherein X is Br of $CF_3$;

wherein $OR_3$ is at the 5- or 8-position and $R_3$ is $(C_1-C_8)$alkyl, $(C_2-C_8)$alkenyl, $-CH_2-(C_3-C_8)$cycloalkyl or benzyl;

wherein $R_7$ is H or $CH_3$;

wherein $R_1$ is $(C_1-C_3)$alkyl or cyclopropylmethyl; and wherein $R_2$ is $-CH_2-(C_3-C_8)$cycloalkyl, $(C_1-C_8)$alkyl, $-(CH_2)_q-R_5$ or $-CH_2CH_2-Z-(CH_2)_rCH_3$, wherein $R_5$ is phenyl, 2-thiophene or 3-thiophene, Z is 0 or S, q is 2 or 3, and r is zero to 3; or a pharmaceutically-acceptable salt thereof.

2. A compound, for therapeutic use, of formula III

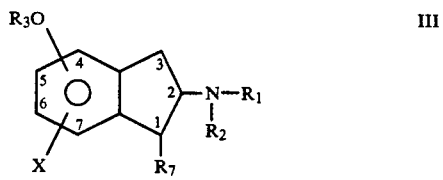

wherein X, $R_1$, $R_2$, $R_3$, $R_7$ are as defined in claim 1, or a pharmaceutically-acceptable acid addition salt thereof.

3. A compound of claim 1, wherein X is Br.

4. A compound of claim 3, wherein $R_2$ is $-CH_2-(C_3-C_8)$cycloalkyl.

5. A compound of claim 2, wherein $R_2$ is $-CH_2-(C_3-C_8)$cycloalkyl.

6. A compound of claim 2, wherein $R_2$ is $(C_1-C_8)$alkyl, $-(CH_2)_q-R_5$ or $-CH_2CH_2-Z(CH_2)_rCH_3$.

7. A compound of claim 1, which is 8-bromo-5-methoxy-2-(di-n-propylamino)tetralin, or cis-1S,2R-8-bromo-5-methoxy-1-methyl-2-(di-n-propylamino)tetralin.

8. A compound of claim 1, which is
5-bromo-8-methoxy-2-(di-n-propylamino)tetralin,
cis-1S,2R-5-bromo-8-methoxy-1-methyl-2-(di-n-propylamino)tetralin,
5-bromo-8-methoxy-2[di(cyclopropylmethyl)amino]tetralin,
(−)-5-bromo-8-methoxy-2[di(cyclopropylmethyl)amino]tetralin.

9. A compound of claim 2, which is 4-bromo-7-methoxy-2-(di-n-propylamino)indane.

* * * * *